(12) United States Patent
Muehlsteff et al.

(10) Patent No.: US 8,870,785 B2
(45) Date of Patent: Oct. 28, 2014

(54) CONTACTLESS RESPIRATION MONITORING OF A PATIENT

(75) Inventors: Jens Muehlsteff, Aachen (DE); Robert Pinter, Lübeck (DE); Geert Guy Georges Morren, Vissenaken (BE)

(73) Assignee: Koninklijke Philips N.V., Eindhoven (NL)

( * ) Notice: Subject to any disclaimer, the term of this patent is extended or adjusted under 35 U.S.C. 154(b) by 1024 days.

(21) Appl. No.: 12/990,806

(22) PCT Filed: May 4, 2009

(86) PCT No.: PCT/IB2009/051800
§ 371 (c)(1),
(2), (4) Date: Jan. 28, 2011

(87) PCT Pub. No.: WO2009/136337
PCT Pub. Date: Nov. 12, 2009

(65) Prior Publication Data
US 2011/0112425 A1    May 12, 2011

(30) Foreign Application Priority Data

May 9, 2008   (EP) ..................................... 08103892

(51) Int. Cl.
| | |
|---|---|
| A61B 5/08 | (2006.01) |
| A61B 5/00 | (2006.01) |
| G01S 13/88 | (2006.01) |
| A61B 5/05 | (2006.01) |
| A61B 5/113 | (2006.01) |
| G01S 13/58 | (2006.01) |
| G01S 7/35 | (2006.01) |

(52) U.S. Cl.
CPC .............. *A61B 5/0816* (2013.01); *A61B 5/7239* (2013.01); *G01S 13/88* (2013.01); *A61B 5/0507* (2013.01); *A61B 5/113* (2013.01); *A61B 5/05* (2013.01); *G01S 13/583* (2013.01); *G01S 7/352* (2013.01)
USPC ....................................................... 600/534

(58) Field of Classification Search
USPC ......... 600/413, 428, 453, 455, 484, 529, 534; 340/539.1, 539.11, 539.12; 324/28, 324/382
See application file for complete search history.

(56) References Cited

U.S. PATENT DOCUMENTS

| | | | |
|---|---|---|---|
| 3,993,995 A | 11/1976 | Kaplan et al. | |
| 4,085,740 A * | 4/1978 | Allen, Jr. ...................... | 600/500 |

(Continued)

FOREIGN PATENT DOCUMENTS

| | | |
|---|---|---|
| WO | 2006115704 A1 | 11/2006 |
| WO | 2007136610 A2 | 11/2007 |

(Continued)

OTHER PUBLICATIONS

Droitcour, Non-Contact Measurement of Heart and Respiration Rates with a Single-Chip Microwave Doppler Radar, Jun. 2006.*

(Continued)

*Primary Examiner* — Jacqueline Cheng
*Assistant Examiner* — Puya Agahi

(57) ABSTRACT

Respiration of a patient is detected by emitting an electromagnetic signal towards the patient; receiving a reflected electromagnetic signal reflected from the patient; converting the reflected electromagnetic signal, yielding a first signal; phase-shifting the reflected electromagnetic signal and converting the phase-shifted reflected electromagnetic signal, yielding a second signal; determining a first vector being defined by the time derivatives of the first signal and the second signal, for a common first point in time; determining a second vector being defined by the time derivatives of the first signal and the second signal, for a common second point in time; and calculating the scalar product of the normalized first vector and the normalized second vector as an indicator value for a change from expiration to inspiration of the patient or vice versa. A change from expiration to inspiration of the patient or vice versa is preferably indicated if the indicator value is below a threshold value, preferably below a value of 0. In this way, respiration is monitored contactlessly and remotely based on the Doppler radar principle which is reliable and easy to handle.

20 Claims, 7 Drawing Sheets

(56) References Cited

U.S. PATENT DOCUMENTS

| | | | |
|---|---|---|---|
| 4,131,889 A | | 12/1978 | Gray |
| 2007/0208212 A1 | | 9/2007 | DiLorenzo |
| 2008/0275337 A1 | | 11/2008 | Fossan et al. |
| 2010/0130873 A1* | | 5/2010 | Yuen et al. .................. 600/484 |
| 2010/0198083 A1* | | 8/2010 | Lin et al. .................... 600/484 |

FOREIGN PATENT DOCUMENTS

| | | | |
|---|---|---|---|
| WO | | 2008026157 A2 | 3/2008 |
| WO | WO 2008026157 A2 * | | 3/2008 |
| WO | | 2008102291 A2 | 8/2008 |

OTHER PUBLICATIONS

Min et al., A study on a non-contacting respiration signal monitoring system using Doppler ultrasound, Sep. 2007, pp. 1113-1119 (hereinafter "Min").*

Muehlsteff et al: "The Use of a Two Channel Doppler Radar Sensor for the Characterization of Heart Motion Phases", Proceedings of the 28th Annual International Conference of the IEEE Engineering in Medicine and Biology Society (EMBS), Aug. 2006, pp. 547-550.

Muehlsteff et al: "A Handheld Device for Simultaneous Detection of Electrical and Mechanical Cardio-Vascular Activities With Synchronized ECG and CW-Doppler Radar"; Proceedings of the 29th Annual International Conference of the IEEE Engineering in Medicine and Biology Society (EMBS), August 2007, pp. 5758-5761.

* cited by examiner

CONTACTLESS RESPIRATION MONITORING OF A PATIENT

FIELD OF THE INVENTION

The invention relates to the field of respiration monitoring of a patient, and especially to a method and a device for reliable breath-to-breath detection of inspiration/expiration for contactless remote respiration monitoring based on the Doppler-Radar principle.

BACKGROUND OF THE INVENTION

In a clinical environment, observing respiratory activity (breathing frequency) is highly relevant. Pulse and respiration are one of the most important basic vital signs to assess the health status of a patient. In intensive care unit (ICU) settings, pulse and respiration are routinely measured via ECG electrodes from the electrocardiogram, and the measured thorax-impedance changes during breathing activity, respectively.

Doppler radar sensors have been identified as a promising technology for contactless measurements of respiration and cardiac activity. A large extent of research activities has been focused on Radar Systems at frequencies above 60 GHz. Today, low-power low-cost Doppler radar sensors are commercially available, mainly for activity detection in homes in the frequency range of <25 GHz. These sensors might be an interesting low-cost solution for remote vital signs monitoring, but they require more efforts in development for intelligent signal analysis, since state-of-the-art signal processing approaches are hardly applicable for these sensors. The main reason is that the wavelengths are large (approx. 10 . . . 120 mm) compared to the motion amplitudes of the thorax caused by respiration and the beating heart.

In Doppler radar sensors, generally, a sender/receiver unit continuously emits electromagnetic waves towards a target. The electromagnetic waves are reflected at the target and travel back to the sender/receiver. Two mixers/receivers are employed in order to evaluate the received signal. The first mixer downconverts the signal received directly at the antenna; the second mixer downconverts the antenna signal after it was phase-shifted by 90 degrees.

A radar sensor has the advantages that no direct skin contact is required. The speed and the direction of movement as well as a change of direction is coded in the measured signals, but especially for operating frequencies <25 GHz, state-of-the-art detection schemes are hardly applicable. Therefore, correct and reliable interpretation of these signals is challenging. However, reliable and comfortable detection of respiration activity in clinical settings is an unmet need today.

SUMMARY OF THE INVENTION

It is an object of the invention to provide a method and device for contactless remote respiration monitoring of a patient based on the Doppler-Radar principle which are reliable and easy to handle.

This object is achieved by a method for detection of respiration of a patient comprising the following steps:
emitting an electromagnetic signal towards the patient;
receiving a reflected electromagnetic signal reflected from the patient using a two-channel Doppler radar sensor;
converting the reflected electromagnetic signal, yielding a first signal;
phase-shifting the reflected electromagnetic signal and converting the phase-shifted reflected electromagnetic signal, yielding a second signal;
determining a first vector being defined by the time derivatives of the first signal and the second signal, for a common first point in time;
determining a second vector being defined by the time derivatives of the first signal and the second signal, for a common second point in time; and
calculating the scalar product of the normalized first vector and the normalized second vector as an indicator value for a change from expiration to inspiration of the patient or vice versa.

Accordingly, it is an important idea of the invention to provide a criterion which allows the detection of the change from expiration to inspiration of the patient or vice versa. This criterion is based on the scalar product of the normalized first vector and the normalized second vector, which are determined by the time derivatives of the first signal and the second signal, for a common first or second point in time, respectively. In this way, an indicator value is provided which allows to detect the direction change of the thorax movements analyzed by Doppler radar sensors, preferably operating at frequencies below 30 GHz in order to provide a breath-to-breath information of expiration and inspiration movement.

The invention provides for several advantages: A reliable measurement of the direction change of the thorax movements during respiration using a two-channel radar can be performed allowing breath-to-breath detection of inspiration/expiration. Further, separate evaluation of inspiration movement and expiration movement can be done. In this way, false alarm rates for remote respiration monitoring can be noticeably reduced. Moreover, increased accuracy of breathing rate detection for remote respiration monitoring based on the Doppler Radar principle is achieved.

Further, the method can be accomplished in a simple way at low costs since a low processing-power method is proposed. There is no need for interpretation of ill-defined Doppler signals morphologies since a well-defined criterion for characterizing the direction of motion is provided, and no need of hardware-defined parameters are required.

For determining the first point in time and the second point in time for building the first vector and the second vector, respectively, according to a preferred embodiment of the invention, characteristic points in time defined by specific criteria fulfilled simultaneously in the first and second signal are determined. Preferably, this specific criteria is a detected zero-crossing of the time derivative of the first signal or the second signal, respectively. Further, according to a preferred embodiment of the invention, the first vector is built by taking the time derivatives of the two signals in the period between a first detected zero-crossing and a second detected zero-crossing, respectively. The second vector is built by taking the time derivatives of the two signals in the period between the second zero-crossing and a detected zero-crossing, respectively. In both cases, the time derivative of the first signal is taken as the first vector coordinate, and the time derivative of the second signal is taken as the second vector coordinate.

In general, the indicator value can be used in different ways in order to detect a change from expiration to inspiration of the patient or vice versa. However, according to a preferred embodiment of the invention, the indicator value is compared with a predefined threshold value. Preferably a threshold value of 0 is used.

In this way, a change from inspiration to expiration or vice versa can be reliably detected since the criterion according to the invention is calculated on the basis of the scalar product of two vectors defined from time derivatives of the measured signals for two different points in time. If the scalar product of the normalized vectors is less than one, the direction of motion has changed and represents different thorax movements of expiration/inspiration. In an ideal case, the vectors are opposite to each other which means that the angle between the vectors is 180° and, thus, the scalar product is −1. In practical applications it will happen, that the respiration movement will not be purely symmetrical. In these cases the vectors will not be exactly opposite of each other, but will show an angle <180°. Accordingly, a minimum of 90° is preferred, being equal to a threshold value of 0. Further, it is preferred that a change from expiration to inspiration of the patient or vice versa is indicated if the indicator value is below the threshold value.

Further, according to a preferred embodiment of the invention, the first vector, the second vector and the scalar product of the normalized first vector and the normalized second vector as an indicator value for a change from expiration to inspiration of the patient or vice versa are consecutively determined, preferably in predefined time periods. In this way, the measured signals can be quasi-continuously scanned for direction changes of the thorax movement.

Furthermore, according to a preferred embodiment of the invention, the vorticity $\vec{V}$ for two different points in time $T_1$ and $T_2$, respectively, are calculated by $$\vec{V}_1 = \vec{r}_1 \times (\vec{M}_1(T_1) - \vec{r}_1) \text{ and } \vec{V}_2 = -\vec{r}_2 \times (\vec{M}_2(T_2) - \vec{r}_2),$$

wherein $\vec{r}_1$ is the first vector, $\vec{r}_2$ is the second vector, and $\vec{M}_1$ and $\vec{M}_2$ are vectors built from the time derivatives of the first signal and the second signal at times T1 and T2, respectively. The voracity depends on the sign of the velocity of the target, i.e. the thorax, and the sensor-target distance. This additional feature is preferably used in order to improve the reliability of the detection, as set out in more detail further below.

Since a two-channel Doppler radar sensor is used, the reflected electromagnetic signal is preferably phase-shifted by 90° before being converted. Further, according to a preferred embodiment of the invention, based on the detected movement changes, the respiration rate of the patient is indicated.

With reference to FIG. 7, above mentioned object is further met by a device 10 for contactless respiration monitoring of a patient, comprising a two-channel Doppler radar sensor 12 for receiving a reflected electromagnetic signal reflected from the patient, wherein the two-channel Doppler radar sensor is adapted for converting the reflected electromagnetic signal, yielding a first signal and for phase-shifting the reflected electromagnetic signal and converting the phase-shifted reflected electromagnetic signal, yielding a second signal; wherein a calculating device 14 is provided which is adapted for determining a first vector being defined by the time derivatives of the first signal and the second signal, for a common first point in time, determining a second vector being defined by the time derivatives of the first signal and the second signal, for a common second point in time, and calculating the scalar product of the normalized first vector and the normalized second vector as an indicator value for a change from expiration to inspiration of the patient or vice versa.

Preferred embodiments of the device according to the invention, in general, relate to the preferred embodiments of the method according to the invention, as described above.

Especially, according to a preferred embodiment of the invention, the calculating device is adapted for comparing the indicator value with a predefined threshold value and for indicating a change from expiration to inspiration of the patient or vice versa is indicated if the indicator value is below the threshold value. Further, it is preferred that a display 16 for displaying the respiration rate based on indicated changes from expiration to inspiration of the patient or vice versa is provided.

It should be emphasized that, though in the present description averaging of measured and/or calculated date is not described in detail, such averaging can be performed in any stage of the processing the data and is understood to be fully covered by the present invention.

Preferred applications of the invention are as follows: spot check contactless respiration effort monitoring in clinical and home settings; continuous contactless respiration rate monitoring in clinical and home settings; stress relaxation; and breathing gating in computer tomography (CT).

BRIEF DESCRIPTION OF THE DRAWINGS

These and other aspects of the invention will be apparent from and elucidated with reference to the embodiments described hereinafter.

In the drawings.

DETAILED DESCRIPTION OF EMBODIMENTS

The two sensor signals coming from a two-channel Doppler radar sensor 12 can be modeled by the following equations:

$$x_1(t) = a \cdot \sum_{k=1}^{N} \frac{1}{D_k(t)^\gamma} \cos(\Theta_k(t)) \tag{1}$$

$$x_2(t) = b \cdot \sum_{k=1}^{N} \frac{1}{D_k(t)^\gamma} \cos(\Theta_k(t) + 2\Phi_1) \tag{2}$$

The cosine factors represent the local amplitudes of the reflected electromagnetic waves. The signal amplitudes a and b differ, because of different sensitivities of the separate channels. The influence of the changing sensor/target distances $D_k(t)$ is modeled by an exponential factor $\gamma$. The phase difference $2\Phi_1$ is determined by the specific Doppler sensor used. The timely varying phase $\Theta_k(t)$ $$\Theta_k(t) = \frac{4\pi}{\lambda}\left(\int_0^t v_k(t')dt' + \Xi_k\right) \quad (3)$$

is related with the Doppler effect as a sum of signals from N reflectors moving with velocity components $v_k(t)$ relevant for the Doppler shift and the sensor/reflector distance $\Xi_k$ for t=0. In the following, a single moving reflector is analyzed, which means that the functions D(t) and Θ(t) are simplified. Sensor/reflector distance D(t) and phase Θ(t) are then linearly related by:

$$D(t) = \frac{\lambda}{4\pi}\Theta(t) - \Xi \quad (4)$$

For a single reflector moving with a constant velocity v, equation (3) is the well-known Doppler-Radar equation.

Figure 1:
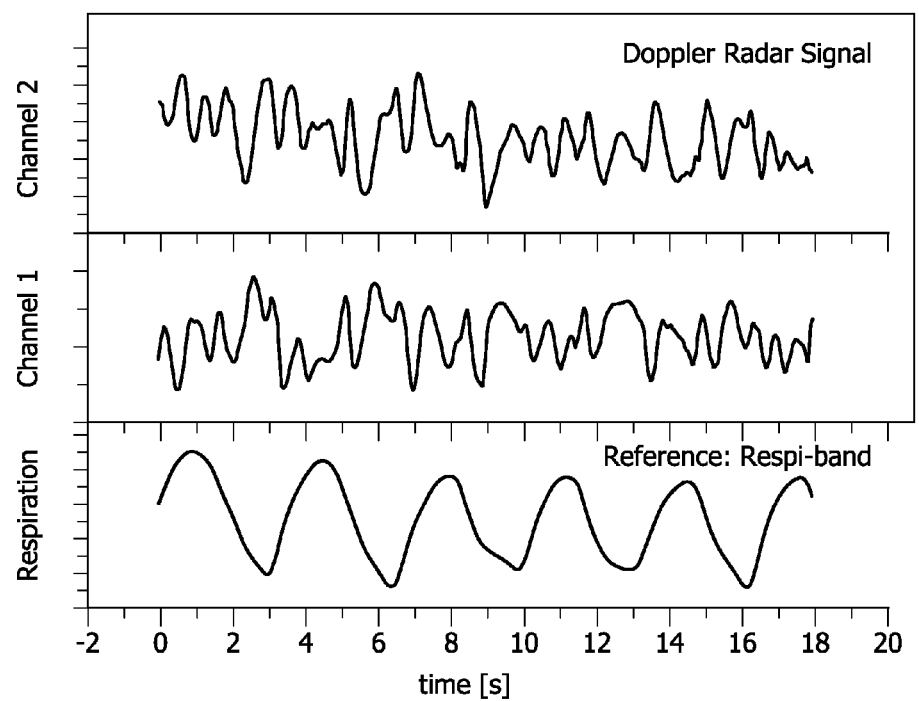
FIG. 1 shows the raw signals of a two Doppler radar sensor measured during tidal breathing and the respiration effort during breathing measured with a respi-band as a reference.

FIG. 1 shows in the upper and middle diagram the raw signals measured with the two-channel Doppler sensor 12 during tidal breathing. The sensor detected the ribcage movement. As a reference, a sensor based on inductive pneumography (respi-band sensor) was used, which is a well-established method for measuring respiration effort and rate. The reference signal is shown in the lower diagram.

As can be seen in the upper and middle diagram the radar signal morphologies are very complex and there is no direct correlation with the reference signal in the lower diagram. The periodicity of the respiration effort sensor cannot be easily derived from the Doppler sensors as well as the movement direction during the breathing cycles. This information cannot be extracted by state-of-the-art schemes in the frequency domain.

According to the preferred embodiment of the invention described in the following, the information on the direction of a movement can be extracted from the two-channel Doppler radar sensor, especially for movements that are small compared to the wavelength λ of the electromagnetic waves. A well-defined criterion is provided, which allows the evaluation of direction change during consecutive detected motion phases.

Figure 2:
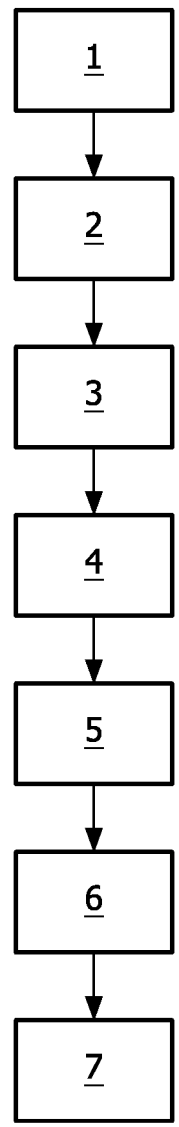
FIG. 2 depicts a flow diagram for detection of direction change during motion under consideration.

FIG. 2 shows the flow diagram with the criterion according to the preferred embodiment of the calculating device 14 in order to improve the accuracy measuring the breathing rate, which assumes the analysis of the predefined time windows covering a number of breathing cycles by a zero-crossing detection scheme. The method for direction change according to this flow diagram is as follows:

Step 1: Detection of point of times $T_i$ of zero-crossings of the time derivative for predefined time window, e.g. 1 minute.

Step 2: Calculation of time differences of consecutively detected zero-crossings: $DT_k = T_{i+1} - T_i$.

Step 3: Checking for criterion of direction change of consecutively detected zero-crossings.

Step 4: Eliminating $DT_k$ not fulfilling criterion.

Step 5: Calculating respiration rate for intervals $RR_k$ from $TD_k$.

Step 6: Eliminating outliers $RR_k$ based on physiological constraints.

Step 7: Calculating average for time window and displaying result.

In the following, the criterion for detection of direction change of movement for two time segments between three detected zero-crossings according to the preferred embodiment of the invention is described. Three detected zero-crossings segment the measured raw signals $x_1$ and $x_2$ into two segments 1 and 2. The criterion is calculated on the basis of the scalar product of two vectors defined from time derivatives of the measured signals $x_1$ and $x_2$ for these two segments 1 and 2. If the scalar product of the normalized vectors is negative, the direction of motion has changed and represents different thorax movements of expiration/inspiration:

$$\frac{\vec{r}_1}{|\vec{r}_1|} \frac{\vec{r}_2}{|\vec{r}_2|} < 0.$$

Based on equations 1, 2, and 3 the time derivative of the signals x1 and x2 are given by:

$$\frac{d}{dt}x_1(t) = A \cdot \frac{4\pi}{\lambda} v \sin(\Theta_k(t))$$

$$\frac{d}{dt}x_2(t) = B \cdot \frac{4\pi}{\lambda} v \sin(\Theta_k(t) + 2\Phi_1)$$

Two vectors are defined for the two segments between three detected zero-crossings via according to:

$$\vec{r}_1 = [<\dot{x}_1>_1 <\dot{x}_2>_1]$$

$$\vec{r}_2 = [<\dot{x}_1>_2 <\dot{x}_2>_2]$$

The first vector r1 is built by taking the time derivatives of the two signals x1 and x2 in the period between the first and second detected zero-crossing. The second vector r2 is built by taking the time derivatives of the two signals x1 and x2 in the period between the second and third detected zero-crossing. In both cases, the time derivative of signal x1 is taken as the first vector coordinate, and the time derivative of signal x2 is taken as the second vector coordinate.

In order to show, that $$\frac{\vec{r}_1}{|\vec{r}_1|} \frac{\vec{r}_2}{|\vec{r}_2|} < 0$$

the vectors r1 and r2 have to be calculated explicitly from equations 1 and 2 for a periodical movement.

Based on the fact that:

$$\int_0^{T1} v \sin(\Theta(t))dt = \frac{\lambda}{4\pi}\cos(\Theta(t))\Big|_0^{T1}$$

$$= \frac{4\pi}{\lambda}\cos\left(\left(\frac{4\pi}{\lambda}\int_0^t v(t')dt' + \Xi\right)\right)\Big|_0^{T1}$$

$$= \frac{4\pi}{\lambda}\left[\cos\left(\frac{4\pi}{\lambda}(\Xi+\delta)\right) - \cos\left(\frac{4\pi}{\lambda}\Xi\right)\right]$$

The same calculation is done for the second period [T1-Tend]. It can be shown that the vector components are given by:

$$\vec{r}_1 \propto \left[\cos\left(\frac{4\pi}{\lambda}(\Xi+\delta)\right) - \cos\left(\frac{4\pi}{\lambda}(\Xi)\right); \sin\left(\frac{4\pi}{\lambda}(\Xi+\delta)\right) - \sin\left(\frac{4\pi}{\lambda}(\Xi)\right)\right]$$

$$\vec{r}_2 \propto \left[\cos\left(\frac{4\pi}{\lambda}\Xi\right) - \cos\left(\frac{4\pi}{\lambda}(\Xi+\delta)\right); \sin\left(\frac{4\pi}{\lambda}\Xi\right) - \sin\left(\frac{4\pi}{\lambda}(\Xi+\delta)\right)\right].$$

Here it is clear for a symmetrical movement, that:

$$r_{x1}=-r_{x2}$$

$$r_{y1}=-r_{y2}.$$

This means, the vectors are opposite to each other, the scalar product is −1 and the angle between the vectors is 180°. In practical applications it will happen, that the respiration movement will not be purely symmetrical. In these cases the vectors will not be exactly opposite to each other, but exhibit an angle <180°. According to the preferred criterion, a minimum of 90° is proposed.

Based on these new axial vectors, the vorticity of axial vectors $r_1$, $r_2$ around these two points—including a change of the basis—for each segment separately, is defined:

$$\vec{V}_1 = -\vec{r}_1 \times (\vec{M}_1(T_1) - \vec{r}_1)$$

$$\vec{V}_2 = -\vec{r}_2 \times (\vec{M}_2(T_2) - \vec{r}_2),$$

where $M_1$ and $M_2$ vectors built from the derivatives of $x_1$ and $x_2$ for the two segments at times $T_1$ and $T_2$ which have to be taken close from the beginning of the movement. These indexes will give a measure of the rotational direction for each movement.

The vorticity vectors depends on the sign of the velocity and the sensor-target distance. This additional feature improves the reliability of the detection.

Figure 3:
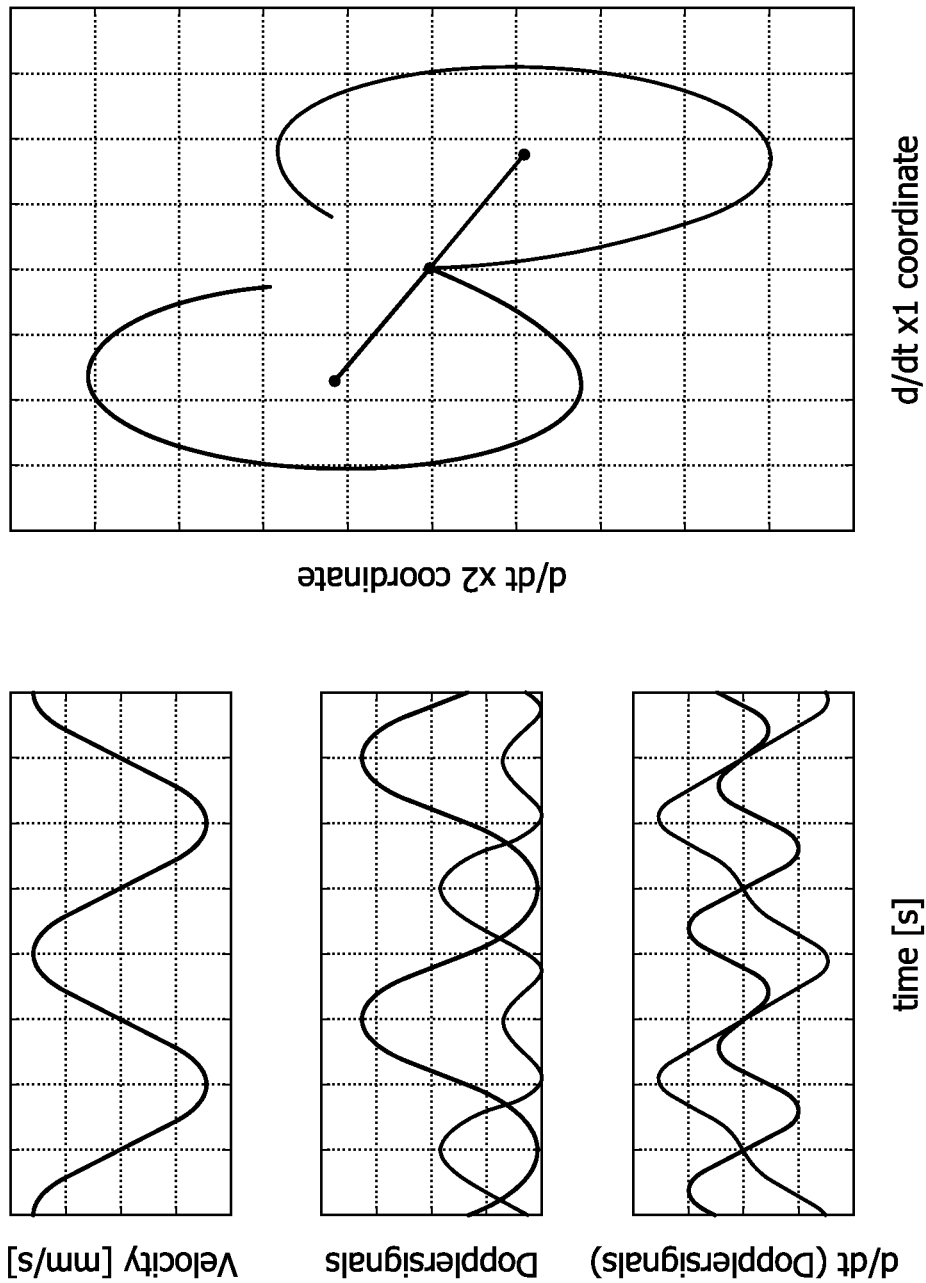
FIG. 3 shows a first simulation of expected Doppler radar signals, time derivatives of both sensor channels and the calculated vectors.
Figure 4:
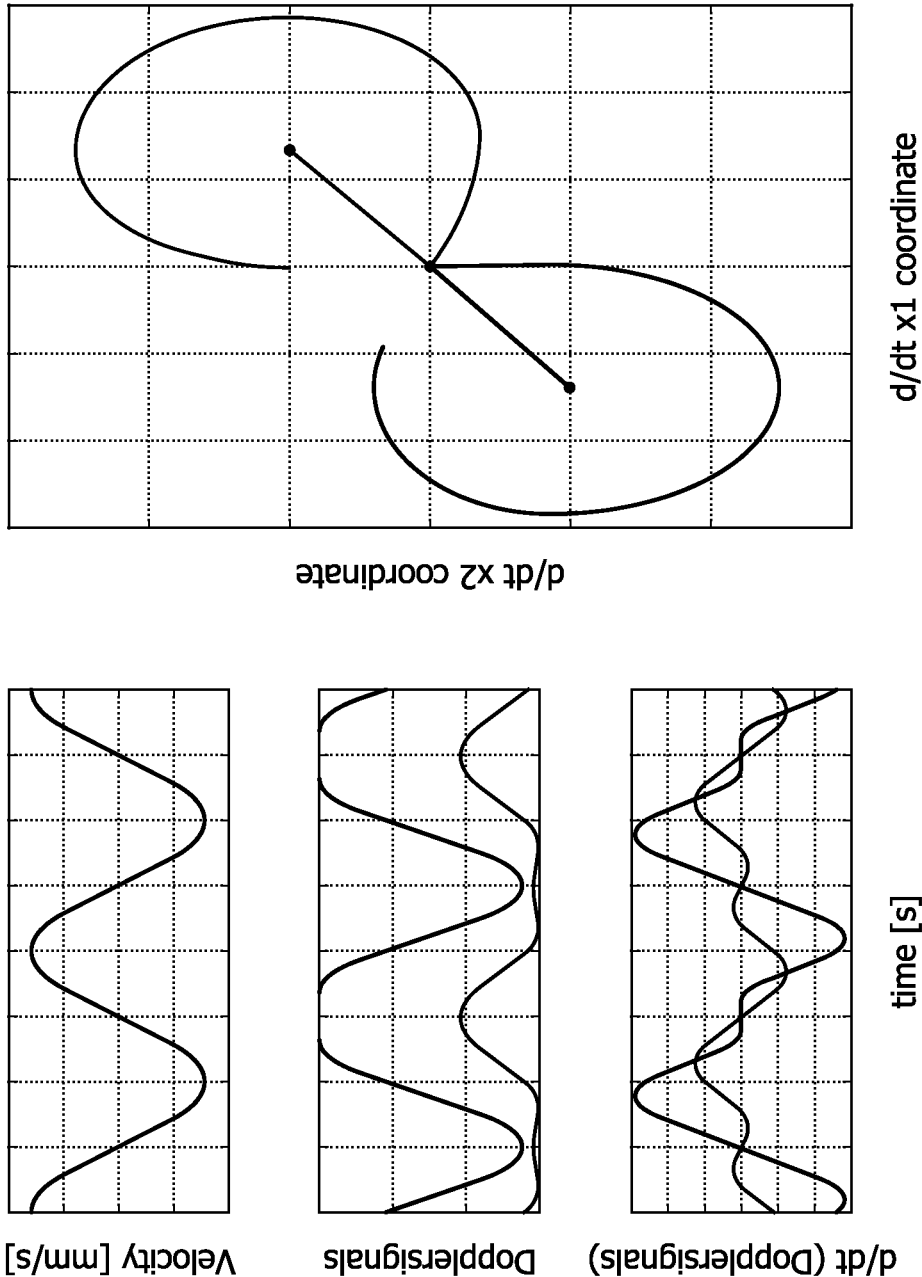
FIG. 4 shows a second simulation of expected Doppler radar signals, time derivatives of both sensor channels and the calculated vectors.

In the following, a numerical simulation for 24 GHz Doppler radar monitoring symmetrical thorax movement is described. FIGS. 3 and 4 show the result of a simulation based on equations 1, 2 and 3. In this case a phase difference of 90° has been assumed between the sensor channels. The thorax velocity was modeled by a cosine-function with a cycle period of 2 s and amplitude of 3 mm/s. The $r_1$, $r_2$ vectors according to the proposed procedure were calculated for the periods [0.5 1.5] and [1.5 2.5] and the vorticity was calculated. The values of the vorticities is shown in the diagram and for better interpretation, within the x-y-plot of the two segments, the traces are shown only from [0.5 1.4] and [1.5 2.4] in order to visualize the "vorticity" around both vectors $r_1$, $r_2$. The vectors $r_1$ and $r_2$ are opposite to each other as well as the sign of the vorticities is different as proposed by the criterion.

Figure 5:
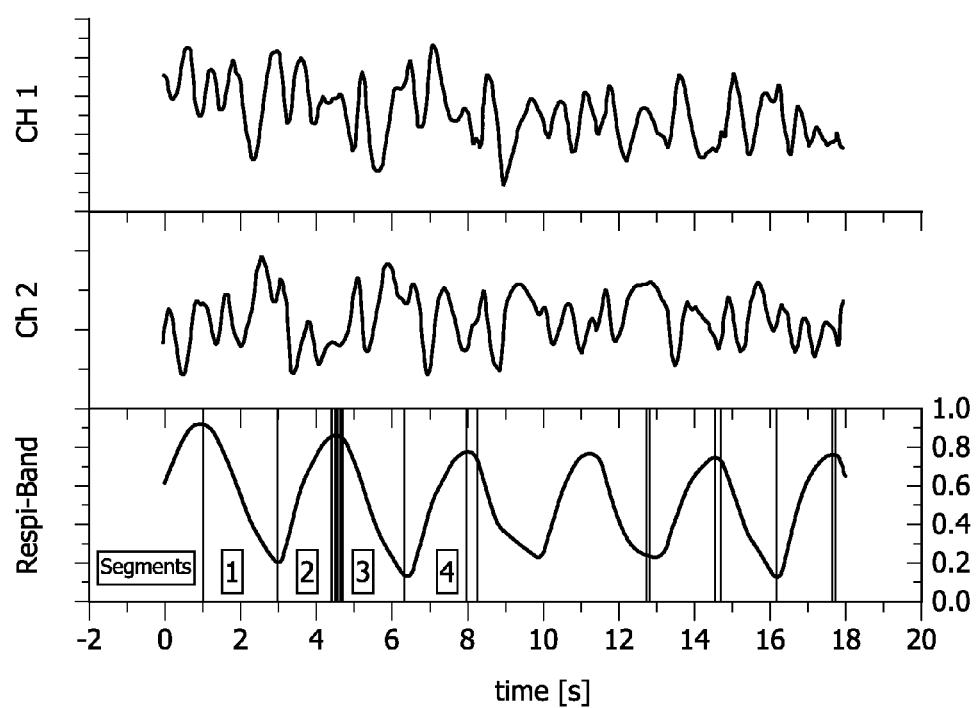
FIG. 5 depicts the detection of zero-crossing according to the criterion of the preferred embodiment of the invention.

In the following, a measurement example for detection of resting phases (step 3 in the flow diagram of FIG. 2) is described. FIG. 5 shows the detection of resting phases from a real measurement. As a reference, a sensor 12 based on inductive plethysmography was used, which is sensitive to detect the changes of thorax circumference (lower diagram). The vertical lines in the lower diagram, which can be displayed on the display device 16, indicate the detected resting points of the thorax change of circumference with this method. Only for the sequence from 8 s to 10 s the respiration cycle was not detected, which might be caused by a thorax movement superpositioned on the respiration movement. More details of the approach for detecting resting phases can be found in "J. Muehlsteff, J. A. J. Thijs, R. Pinter, The use of a two-channel Doppler Radar Sensor for the detection of heart motion phases, 2006, IEEE EMBC 2006, Conference Proceedings" which is incorporated herein by reference.

Figure 6:
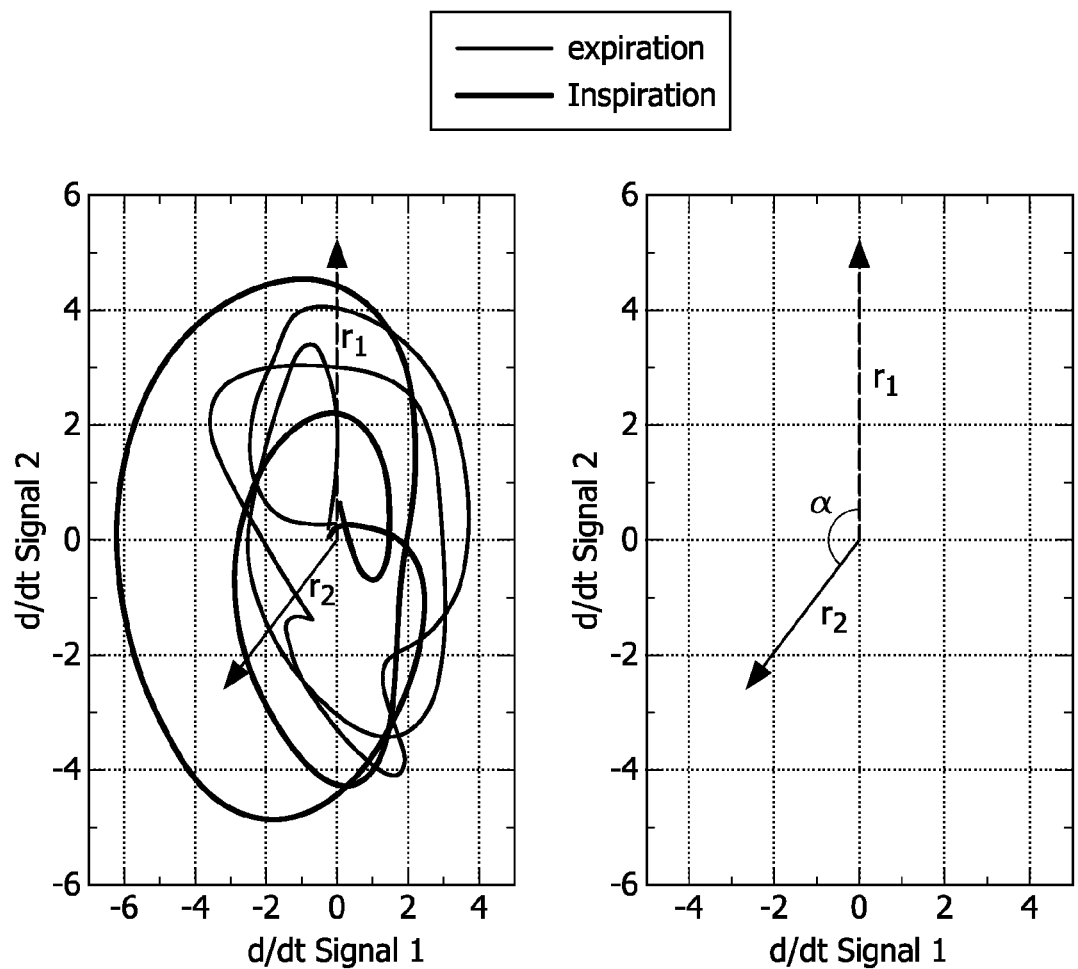
FIG. 6 shows a x-y plot of the derivatives of the signal from FIG. 2 for segments 1 and 2.
Figure 7:
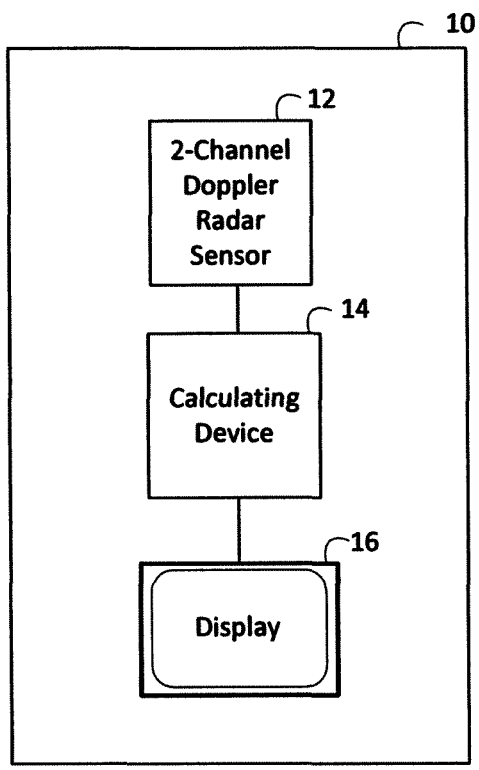
FIG. 7 is a diagrammatic illustration of a system for performing the method.

The approach for detecting motion directions for segments 1 to 2 of FIG. 3 is as follows:

In FIG. 6 the concept for motion direction is shown, e.g. displayed on the display device 16 for the segments 1 and 2 of the data of FIG. 5. In the left diagram the x-y-plot of the time derivatives of the raw signals are shown from which the vectors were calculated according to the proposed method. As can be seen in the right diagram of FIG. 6 the angle between the vectors is greater than 90° and indicates that the two consecutive segments represent different motion directions, therefore represent expiration and inspiration activity.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. A method for detection of respiration of a patient comprising the following steps:
    emitting using a two-channel Doppler radar sensor an electromagnetic signal towards the patient;
    receiving a reflected electromagnetic signal reflected from the patient using the two-channel Doppler radar sensor;
    converting using the two-channel Doppler radar sensor the reflected electromagnetic signal to a first signal;
    phase-shifting using the two-channel Doppler radar sensor the reflected electromagnetic signal and converting the phase-shifted reflected electromagnetic signal to a second signal;
    determining using a calculating device a first vector by taking time derivatives of the first signal and the second signal, for a common first point in time;
    determining using the calculating device a second vector by taking the time derivatives of the first signal and the second signal, for a common second point in time;
    normalizing using the calculating device the first and second vectors;
    calculating using the calculating device the scalar product of the normalized first vector and the normalized second vector as an indicator value for a change from expiration to inspiration of the patient or vice versa; and
    controlling a display to display a respiration value based on the indicated changed from expiration to inspiration of the patient or vice versa.

2. The method according to claim 1, further including:
    determining the first point in time and the second point in time for building the first vector and the second vector by determining, respectively, characteristic points in time defined by specific criteria fulfilled simultaneously in the first signal and the second signal.

3. The method according to claim 2, wherein the specific criteria is a detected zero-crossing of the time derivative of the first signal or the second signal, respectively.

4. The method according to claim 1, wherein an indicator value is compared within a predefined threshold value.

5. The method according to claim 4, wherein the predefined threshold value is 0.

6. The method according to claim 4, wherein the change from expiration to inspiration of the patient or vice versa is indicated using the display if the indicator value is below the predefined threshold value.

7. The method according to claim 1, wherein the first vector, the second vector and the scalar product of the normalized first vector and the normalized second vector as an indicator value for the change from expiration to inspiration of the patient or vice versa are consecutively determined, preferably in predefined time periods.

8. The method according to claim 1, wherein calculating includes calculating a vorticity $\vec{V}$ for the first point in time $T_1$ and the second point in time $T_2$, respectively, by $\vec{V}_1 = -\vec{r}_1 \times (\vec{M}_1(T_1) - \vec{r}_1)$ and $\vec{V}_2 = -\vec{r}_2 \times (\vec{M}_2(T_2) - \vec{r}_2)$, wherein $\vec{r}_1$ is the first vector, $\vec{r}_2$ is the second vector, and $\vec{M}_1$ and $\vec{M}_2$ are vectors built from the time derivatives of the first signal and the second signal at times $T_1$ and $T_2$, respectively.

9. The method according to claim 1, wherein a respiration rate is indicated.

10. A device for contactless respiration monitoring of a patient, comprising:
   a two-channel Doppler radar sensor configured to:
      receive a reflected electromagnetic signal reflected from the patient,
      convert the reflected electromagnetic signal to a first signal,
      phase-shift the reflected electromagnetic signal, and
      convert the phase-shifted reflected electromagnetic signal to a signal; and
   a calculating unit configured to:
      determine a first vector defined by taking time derivatives of the first signal and the second signal, for a common first point in time,
      determine a second vector defined by taking time derivatives of the first signal and the second signal, for a common second point in time,
      normalize the first and second vectors,
      calculate a scalar product of the normalized first vector and the normalized second vector as an indicator value for a change from expiration to inspiration of the patient or vice versa, and
      control a display to display a respiration value based on the indicated changed from expiration to inspiration of the patient or vice versa.

11. The device according to claim 10, wherein the calculating unit is further configured to:
   compare the indicator value with a predefined threshold value, and
   indicate using the display the change from expiration to inspiration of the patient or vice versa in response to an indicator value being below the predefined threshold value.

12. The device according to claim 10, further including:
   the display configured for displaying a respiration rate based on indicated changes from expiration to inspiration of the patient or vice versa.

13. A contactless respiration monitoring system for monitoring respiration of a patient, comprising:
   an emitter adapted to emit an electromagnetic signal towards the patient;
   a two-channel Doppler radar sensor adapted to:
      receive a reflected electromagnetic signal reflected from the patient;
      convert the reflected electromagnetic signal to a first signal; and
      phase-shift the reflected electromagnetic signal; and
      convert the phase-shifted reflected electromagnetic signal to a second signal;
   a calculating unit adapted to:
      determine a first vector defined by taking a time derivative of the first signal taken in a first period of time as a first vector coordinate of the first vector, and a time derivative of the second signal taken in the first period of time as a second vector coordinate of the first vector;
      determine a second vector defined by taking a time derivative of the first signal taken in a second period of time as a first vector coordinate of the second vector, and a time derivative of the second signal taken in the second period of time as a second vector coordinate of the second vector;
      calculate the scalar produce of the normalized first vector and the normalized second vector as an indicator value for a change from expiration to inspiration of the patient or vice versa; and
      control a display to display a respiration value based on the indicated changed from expiration to inspiration of the patient or vice versa.

14. The system according to claim 13, wherein the calculating unit is further adapted to:
   determine characteristic points in time defined by specific criteria fulfilled simultaneously in the first signal and the second signal.

15. The system according to claim 14, wherein the specific criteria includes a detected zero-crossing of the time derivative of the first signal or the second signal, respectively.

16. The system according to claim 13, wherein an indicator value is compared with a predefined threshold value.

17. The system according to claim 16, wherein the change from expiration to inspiration of the patient or vice versa is indicated using the display if the indicator value is below the predefined threshold value.

18. The system according to claim 13, wherein the first vector, the second vector and the scalar product of the normalized first vector and the normalized second vector as an indicator value for the change from expiration to inspiration of the patient or vice versa are consecutively determined, preferably in predefined time periods.

19. The system according to claim 13, wherein the calculating unit is further adapted to calculate a vorticity $\vec{V}$ for the first period of time $T_1$ and the second period of time $T_2$, respectively, by $\vec{V}_1 = -\vec{r}_1 \times (\vec{M}_1(T_1) - \vec{r}_1)$ and $\vec{V}_2 = -\vec{r}_2 \times (\vec{M}_2(T_2) - \vec{r}_2)$, wherein $\vec{r}_1$ is the first vector, $\vec{r}_2$ is the second vector, and $\vec{M}_1$ and $\vec{M}_2$ are vectors built from the time derivatives of the first signal and the second signal at times $T_1$ and $T_2$, respectively.

20. The system according to claim 13, wherein a respiration rate is indicated using the display.

* * * * *